(12) United States Patent
Nold et al.

(10) Patent No.: US 9,851,396 B2
(45) Date of Patent: Dec. 26, 2017

(54) INSTRUMENT TEST ARRANGEMENT

(71) Applicant: ERBE ELEKTROMEDIZIN GMBH, Tuebingen (DE)

(72) Inventors: Bernhard Nold, Tuebingen (DE); Matthias Zenker, Tuebingen (DE); Peter Selig, Hechingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 94 days.

(21) Appl. No.: 14/518,240

(22) Filed: Oct. 20, 2014

(65) Prior Publication Data
US 2015/0108995 A1 Apr. 23, 2015

(30) Foreign Application Priority Data
Oct. 21, 2013 (EP) ..................... 13189566

(51) Int. Cl.
*G01R 31/02* (2006.01)
*G01R 31/28* (2006.01)
*A61B 18/18* (2006.01)
*A61B 18/04* (2006.01)
*A61B 18/16* (2006.01)
(Continued)

(52) U.S. Cl.
CPC ........ *G01R 31/2829* (2013.01); *A61B 18/042* (2013.01); *A61B 18/18* (2013.01); *G01R 31/025* (2013.01); *A61B 18/16* (2013.01); *A61B 2017/00477* (2013.01);
(Continued)

(58) Field of Classification Search
CPC G01R 31/2829; G01R 31/025; A61B 18/042; A61B 18/18; A61B 18/16; A61B 2017/0047; A61B 2017/00725; A61B 2018/00589
See application file for complete search history.

(56) References Cited

U.S. PATENT DOCUMENTS 6,565,558 B1 * 5/2003 Lindenmeier ........ A61B 18/042
604/22
8,157,795 B2 * 4/2012 Sartor .................. A61B 18/042
606/41
(Continued)

FOREIGN PATENT DOCUMENTS

CN 1984614 A 6/2007
CN 200996894 Y 12/2007
(Continued)

*Primary Examiner* — Tung X Nguyen
*Assistant Examiner* — Douglas X Rodriguez
(74) *Attorney, Agent, or Firm* — Blank Rome LLP

(57) ABSTRACT

An instrument test arrangement is specified, which is preferably equipped for medical instruments for argon plasma coagulation. The instrument test arrangement comprises an electrode arrangement, comprising at least one test electrode. In a preferred embodiment, a test electrode is thereby connected to two neutral conductors of a neutral conductor cable or device, wherein the neutral conductors are insulated from one another, and wherein the first coupling impedance between the test electrode and the first neutral conductor and the second coupling impedance between the test electrode and the second neutral conductor are equal or at most slightly different, so that a split circuit, which is assigned to a neutral electrode arrangement, does not trigger due to the strike of a test spark or arc.

13 Claims, 7 Drawing Sheets

(51) Int. Cl.
    *A61B 17/00*         (2006.01)
    *A61B 18/00*         (2006.01)

(52) U.S. Cl.
    CPC ............... *A61B 2017/00725* (2013.01); *A61B 2018/00589* (2013.01); *A61B 2018/00875* (2013.01)

(56) References Cited

U.S. PATENT DOCUMENTS

2012/0323236 A1   12/2012  Hagg et al.
2015/0041172 A1*  2/2015  Gareis ...................... D04C 1/06
                                                                         174/34

FOREIGN PATENT DOCUMENTS

| CN | 101160103 A | 4/2008 |
|---|---|---|
| DE | 198 39 826 A1 | 3/2000 |
| EP | 1 693 014 A1 | 8/2006 |
| EP | 1 764 057 A1 | 3/2007 |
| EP | 2 537 479 A1 | 12/2012 |
| JP | 2012-223585 | 11/2012 |
| WO | WO 2006/077567 A1 | 7/2006 |
| WO | WO 2013/139945 A1 | 9/2013 |

\* cited by examiner

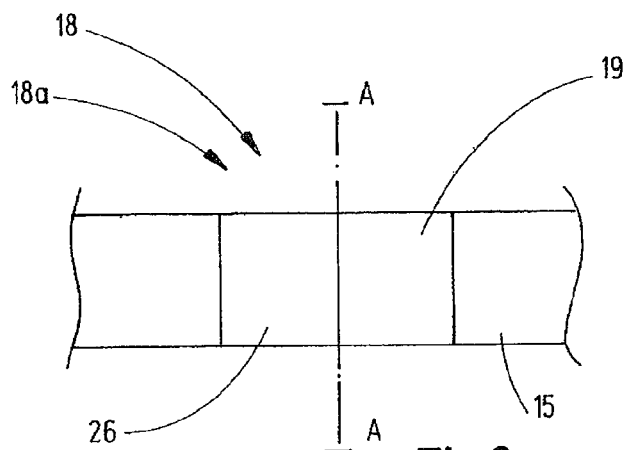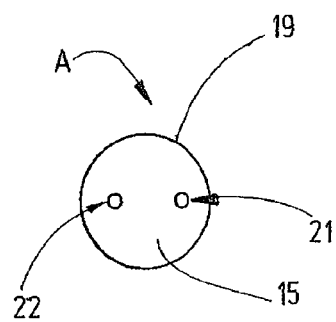
Fig. 3a  Fig. 3b
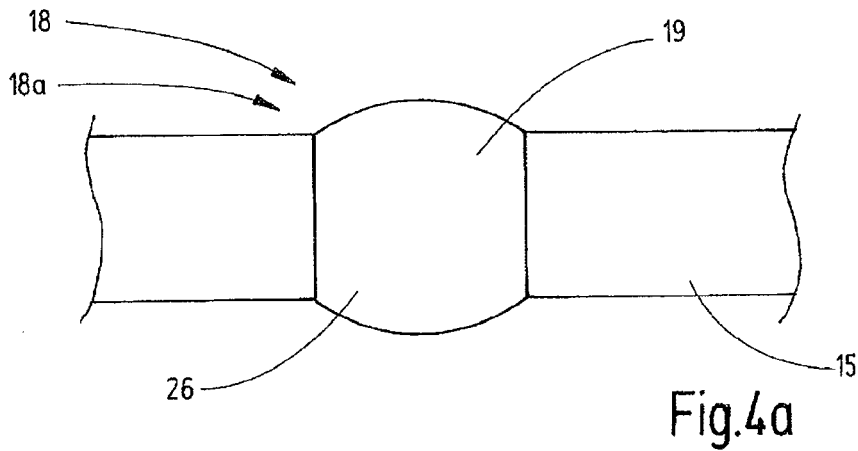
Fig. 4a
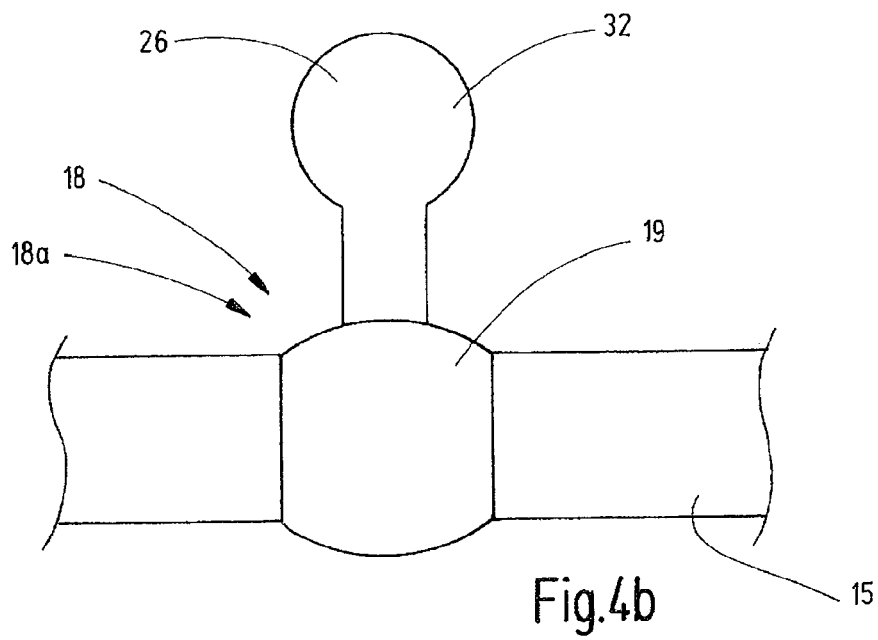
Fig. 4b

INSTRUMENT TEST ARRANGEMENT

TECHNICAL FIELD

Embodiments of the invention relate to an instrument test arrangement, in particular for medical instruments for argon plasma coagulation.

BACKGROUND

Metal parts of equipment of the operating room, against which the user tests the spar striking ability of the coagulation instrument, are locations, which are common in day-to-day operations. Due to such an inadmissible testing at any metal parts, which are connected to the neutral electrode via certain conductance and/or a capacitance, injuries to patient and personnel as well as damages to electrical and electronic devices are possible.

Argon plasma coagulation instruments are fed by a RF generator to create a spark. Prior to using the coagulation instrument on the patient, it is often desired to test the operability, in particular the spar striking ability of the coagulation instrument, in that a test spark is generated.

An adapter plug, which is to be inserted in the electrical circuit between the neutral conductor connection of the generator and the neutral plug of the patient electrode, is known from EP 1 764 057 A1. This spark striking test adapter comprises a conductive area, at which the plasma-surgical instrument can be tested for function. Provision can be made between the conductive area and the neutral conductor of the plug for a resistor.

SUMMARY

Based on this, it is an object of embodiments of the invention to specify a concept, by means of which the operability, in particular the arc or spark striking ability of an instrument or of a probe can be tested prior to being used on the patient in a comfortable manner.

This object is solved by means of an instrument test arrangement, by means of which the operability of a medical RF-surgical instrument, in particular of an instrument for argon plasma coagulation, can be tested safely.

The instrument test arrangement can be embodied as modified neutral conductor cable, as additional part to a neutral conductor cable, for example as attachment or as plug adapter. It can also be embodied at the neutral electrode connection or at the feeding device itself.

The instrument test arrangement comprises an electrode arrangement comprising at least one arc or spark striking test electrode. The neutral conductor cable or the device comprises at least two neutral conductors, which are insulated from one another and via which the neutral electrode patches, which are to be attached to the patient, are connected. Preferably, the spark striking test electrode is connected electrically to at least two neutral conductors of a neutral conductor cable or of a device.

The instrument test arrangement can comprise a single spark striking test electrode or two or more spark striking test electrodes. A spark striking test electrode of the instrument test arrangement can be comprised of a plurality of sections or parts, which are connected to one another galvanically. The sections or parts of the spark striking test electrode can be connected to one another in particular so as to be firmly wired or so as to conduct direct current. Such a connection can be created after the production of the sections or parts of the spark striking test electrode, for example by means of a wire connection. A one-piece spark striking test electrode can encompass material webs or sections, which connect different sections of the spark striking test electrode to one another. From the perspective of the spark, a spark striking test electrode comprising a plurality of sections or parts, which are connected to one another, can present itself as a plurality of spark striking test electrodes.

The electrical connection of the spark striking test electrodes to the neutral conductors, that is, the electrical coupling, comprises a capacitive and/or resistive characteristic, for example. A coupling, in particular a capacitive coupling, can be created for example in that the spark striking test electrode surrounds the neutral conductor cable or is arranged least in sections along the periphery and/or the longitudinal extension of the neutral conductor cable, preferably at a fixed distance thereto. Discrete capacitive devices or components between the neutral conductor and the spark striking test electrode can thus be foregone, if necessary. Together with the spark striking test electrode, the neutral conductors form a capacitor arrangement with the insulating material of the cable as dielectric.

The spark striking test electrode can be a metallic ring or a sleeve, for example, which surrounds the neutral conductor cable. The ring can rest on the neutral conductor cable, for example, or can be incorporated in the cable insulation. In this case, the spark striking test electrode can couple capacitively to the neutral conductors through the cable insulation as dielectric. The spark striking test electrode can also be embodied as or can comprise a protruding sphere.

The spark striking test electrode can be a metal foil. Such a metal foil can be applied to the neutral conductor cable, for example by means of adhesion. The spark striking test electrode can be formed by means of a metallization or by means of a metal coating, for example of a neutral conductor cable section or of a housing of an instrument test arrangement, which is embodied as plug adapter. The metallization or coating can be applied around or onto the neutral conductor cable, respectively, e.g. in a ring-shaped, helical or strip-shaped manner. For example, the cable jacket can be metallized or coated on the outside at least in sections. A helical spark striking test electrode can also be formed by means of a bent metal strip or wire, for example, which is arranged so as to wind around the neutral conductor cable.

Preferably, the instrument test arrangement comprises a test surface, which is assigned to the spark striking test electrode. For example, the test surface can be a surface of the spark striking test electrode. The user of the surgical instrument brings the instrument into the vicinity of or against the test surface, so as to test the spar striking ability and other operability of the instrument, which the user can determine by means of a spark, which strikes from the instrument to the test surface. In a preferred embodiment, the test surface is convex, that is, it is curved outwards, or the test surface comprises a convex section.

The test surface and/or the spark striking test electrode is preferably arranged on or at a convex support. Due to the arrangement at a support, which is curved outwards, the spark striking test electrode or the test surface, respectively, can be accessed in a particularly simple manner and can be cleaned easily. A spark striking test electrode comprising a convex test surface can be created by means of a spherical or spherical segment-shaped appendage or attachment, for example.

In a preferred embodiment, the spark striking test electrode comprises a cohesive test surface. A surface, which can be cleaned particularly well, is created by embodying the test surface without any interruptions.

The spark striking test electrode, which is attached to a cable, can be embodied so as to be flexible, e.g. in that it is embodied as metallic gauze hose, which surrounds the neutral conductor cable at least in sections. The spark striking test electrode can be arranged on the neutral conductor in a displaceable or stationary manner.

Preferably, a split circuit is arranged between the neutral conductors. Said split circuit serves the purpose of measuring the ohmic resistance or the impedance, which prevails between the electrode patches of the neutral electrode, so as to verify the correct attachment of the electrode patches on the patient. Preferably, the spark striking test electrode couples to the respective neutral conductors with the same impedances or with an impedance, which is at most slightly different. An impedance difference, which is only slight, refers to a difference, which does not result in currents in the neutral conductors, which are different to the extent that the split circuit triggers, thus erroneously indicates a lack of contact of the electrode patches of the neutral electrode to the body of the patient when HF energy is applied to the spark striking test electrode.

The spark striking test electrode can be connected to the neutral conductor by means of a discrete component, which comprises an impedance. For example, the spark striking test electrode can be connected to a first neutral conductor by means of a first component, which comprises an impedance, and can be connected to a second neutral conductor by means of a second component, which comprises an impedance. The impedances of the components are preferably equal or are at most slightly different as indicated above. A component can be a linear or non-linear resistor or a capacitive component, for example. Components comprising an ohmic and capacitive portion of the impedance or semiconductor components can also be used. To attain a coupling of the spark striking test electrode to the respective neutral conductors comprising the same impedances or an impedance, which is at most slightly different, the components preferably comprise the same electrical characteristic values for coupling to the respective neutral conductor.

In an embodiment, two neutral conductors are connected to one another via a serial arrangement of two capacitances, wherein the spark striking test electrode is contacted electrically between the two capacitances.

Preferably, the total capacitance between the neutral conductors in the instrument test arrangement, for example in a form, which is embodied as plug adapter or connector of the neutral conductor cable, is less than or equal to 1 nF. Preferably, the additional capacitance between the neutral conductors, which is generated between the spark striking test electrode and neutral conductors by means of coupling capacitances, is less than or equal to 1 nF. Preferably, the instrument test arrangement only contributes to the capacitance between the neutral conductors to an extend that, in addition to the possibility of carrying out a spark striking test, an impedance measurement between the electrode patches makes it possible to reliably determine that the electrode patches of the neutral electrode are attached to the body of the patient. In particular, the instrument test arrangement is preferably compatible with a corresponding split circuit.

Further details of advantageous embodiments of the invention are the subject matter of claims, the description and/or the drawings.

BRIEF DESCRIPTION OF THE DRAWINGS

FIGS. 3a, 3b show views of the instrument test arrangement according to an embodiment of the invention comprising a ring-shaped spark striking test electrode, FIGS. 4a, 4b, 5 show further embodiments of the instrument test arrangement.

DETAILED DESCRIPTION

Figure 1:
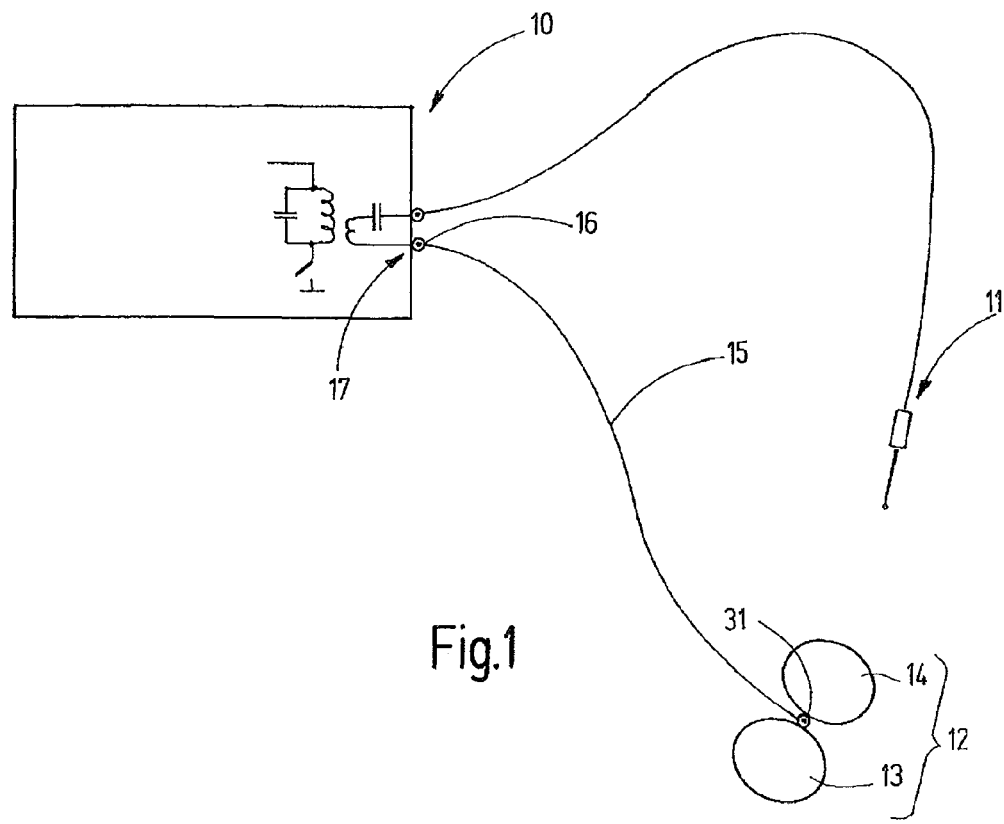
FIG. 1 shows a medical device for feeding an HF-surgical instrument as well as a neutral conductor cable for connecting a neutral conductor arrangement to the device in schematic illustration.

FIG. 1 illustrates a medical device 10 for feeding an electro-surgical instrument 11, which acts on biological tissue. The instrument 11 can be an instrument, which is used in open surgery, for laparoscopy or also for endoscopy, e.g. a so-called probe. In particular, the instrument 11 can be an argon plasma coagulation probe.

The current, which is introduced into the biological tissue by means of the instrument 11, is returned to the device 10 via a neutral electrode arrangement 12. The neutral electrode arrangement 12 comprises two or more electrode patches 13, 14, which belong to a neutral conductor cable 15 or which are connected to the latter. The neutral conductor cable 15 establishes a flexible connection between the neutral electrode arrangement 12 and the device 10. At its end on the device side, the neutral conductor cable 15 comprises a connector 16, which is plugged into the neutral socket 17 of the device 10.

Figure 2:
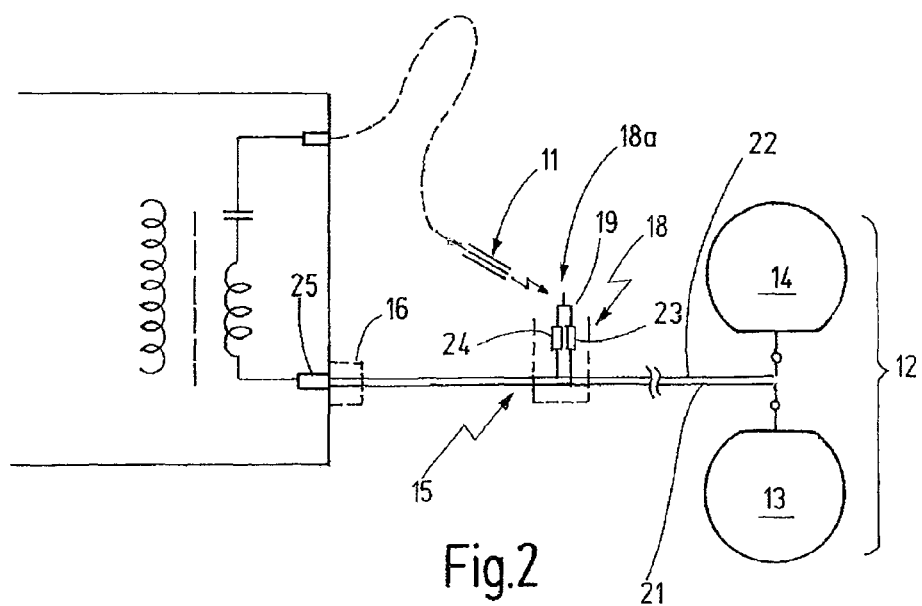
FIG. 2 shows an instrument test arrangement according to an embodiment of the invention.

As is shown in FIG. 2, the neutral conductor cable 15 can be provided with an instrument test arrangement 18, which serves the purpose of being able to test the spark or arc striking ability and operability of the instrument 11.

The instrument test arrangement 18 comprises a spark striking test electrode 19, which is connected electrically to a first neutral conductor 21 as well as to a second neutral conductor 22 of the neutral conductor cable 15. The first neutral conductor 21 and the second neutral conductor 22 are insulated from one another, so that direct current is not conducted between them. The spark striking test electrode 19 is connected to the neutral conductor 21 via a first impedance component 23, for example a capacitive or also via a resistive, e.g. an ohmic component. The spark striking test electrode 19 is furthermore connected to the second neutral conductor 22 via a second impedance component 24. Preferably, the impedances of the impedance components 23, 24 are the same.

The neutral conductor 21 is connected to the first electrode patch 13 and the neutral conductor 22 is connected to the second electrode patch 14. A split circuit 25 is only suggested schematically in FIG. 2 and serves the purpose of measuring the ohmic resistance or the impedance between the two electrode patches 13, 14. It is detected in this manner, whether both electrode patches 13, 14, and thus the entire neutral electrode arrangement 12, comprises a sufficient electrical contact to the patient.

The device 10 and the instrument 11 as well as in particular the instrument test arrangement 18 operate as follows:

To carry out a treatment with the instrument 11, the latter is initially connected to the device 10, as is illustrated in FIG. 1. In addition, the neutral electrode arrangement 12 is attached to the human or animal patient. The user will then want to test the operability and in particular the sparc or arc striking ability of the instrument 11. For this purpose, the user brings the distal end of the probe or of the instrument 11 into the vicinity of the spark striking test electrode 19 or of a test surface 26, respectively (FIG. 3), which comprises the spark striking test electrode 19, and then activates the generator of the device 10. If the instrument 11 is operable, a spark strikes the test electrode 19. The current, which flows as an experiment, flows via both conductors 21, 22 to the device 10 in approximately even proportions. The neutral electrode arrangement 12 remains on uniform, freely-floating potential. A potential difference is not created between both electrode patches. Due to the even current sharing, the split circuit 25 does not detect an error signal. It sees the same conditions as in the case of surgery or treatment at the patient.

Figure 2A:
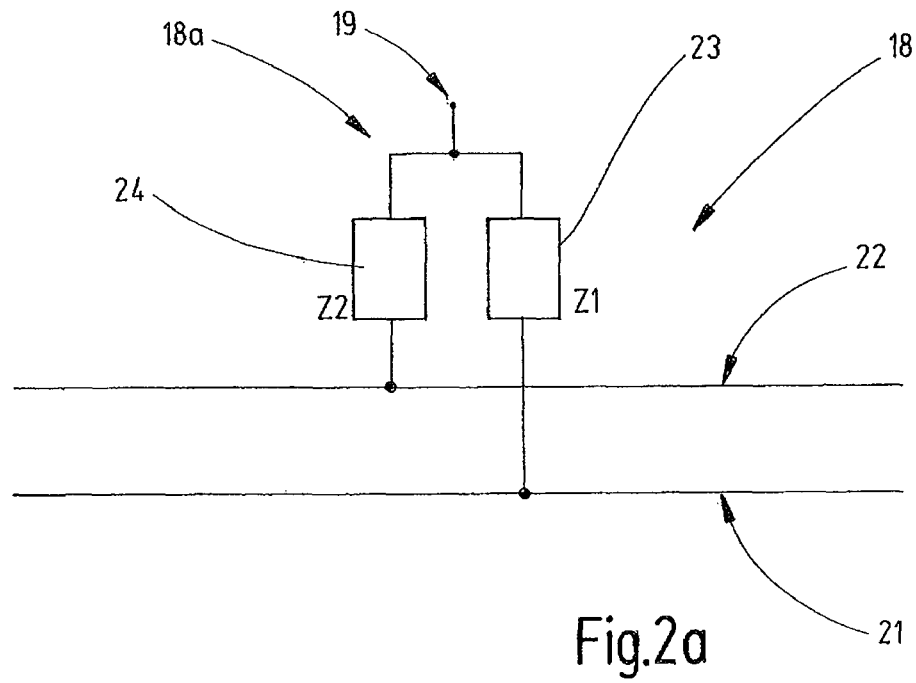
FIGS. 2a, 2b show an illustration of the coupling of the spark striking test electrode to the neutral conductor according to an instrument test arrangement according to an embodiment of the invention.
Figure 2B:
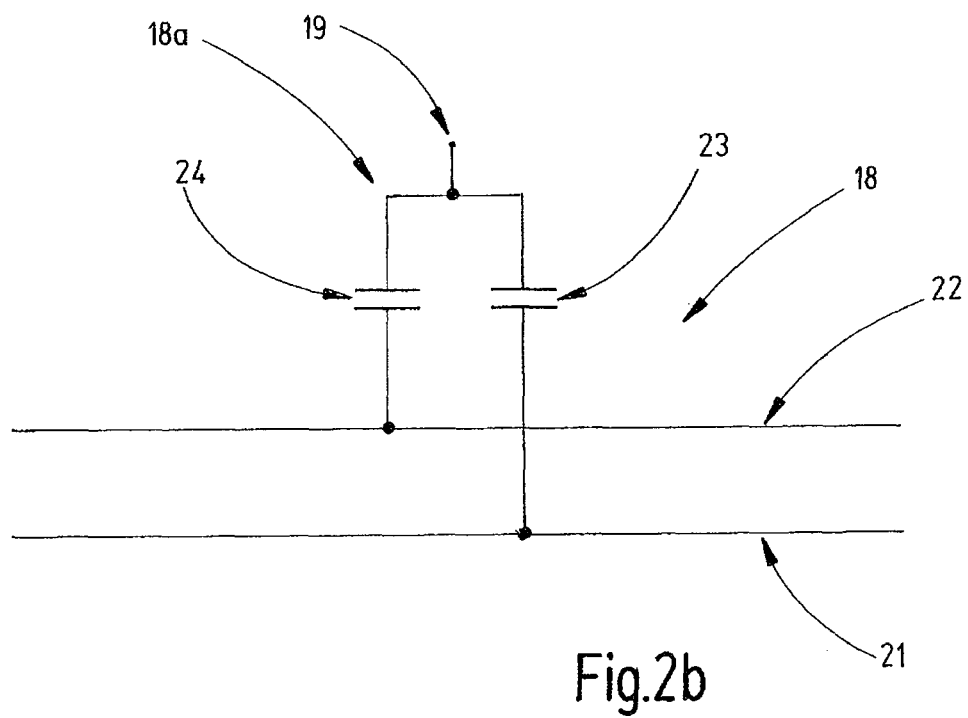

FIG. 2a illustrates the instrument test arrangement 18 from FIG. 2 in a general manner. The test electrode 19 comprises a connection to the first neutral conductor 21 as well as a connection to the second neutral conductor 22. The connection of the test electrode 19 to the first neutral conductor 21 or to the second neutral conductor 22, respectively, is characterized by a first impedance 23 (Z1) or a second impedance 24 (Z2), respectively. These impedances can be realized by means of discrete electrical components, as in the exemplary embodiment according to FIG. 2. In an exemplary and preferable manner, a capacitive coupling as in the instrument test arrangement in FIG. 2b, however, can also be formed by the capacitance, which is formed between a metallic element at the neutral conductor cable 15 and the neutral conductors 21, 22 thereof, conveyed by the cable insulation as dielectric.

The metallic element can be embodied as ring around the neutral conductor cable 15, as is illustrated in context with FIG. 3. Due to the cable insulation, the ring couples capacitively to the first neutral conductor 21 as well as to the second neutral conductor 22.

Regardless of whether the capacitive coupling between the test electrode 19 and the neutral conductors 21, 22 is formed by discrete components (capacitors) or by the stray capacitance between the test electrode 19 and the neutral conductors 21, 22, the capacitance is low. Preferably, the additional capacitance between the neutral conductors 21, 22 is maximally 10 nF, more preferably only 5 nF and, at best, maximally 1 nF. Preferably, the capacitance is calculated to be so low that the impedance formed by the capacitance has a current-limiting effect, so as to prevent dangerous or even only uncomfortable electrical flow through the surgical staff. If, on the one hand, a person touches the patient at the site of the surgery or a metallic element at ground potential and, on the other hand, the test electrode 19, the current through the person is limited to a non-dangerous level, because the capacitance is that small. Preferably, the impedance is larger than 400 V/A.

Regardless of the design of the coupling of the test electrode to the neutral conductors, the impedances of the test electrode 19 to the neutral conductors 21, 22 are preferably equal or at most slightly different. In this manner, a test spark does not lead to a triggering of the slit circuit 25.

To embody an instrument test arrangement 18, a ring-shaped test electrode 19 can be pulled over the neutral conductor cable 15, which is illustrated in FIG. 3a. The ring-shaped test electrode 19 is preferably closed in a ring-shaped manner, but can also be intermittent. The test electrode 19 can be a metal ring or a metal foil or a metal coating, for example a metallization or a vaporization of the neutral conductor cable with metal. Due to the fact that the ring-shaped test electrode 19 comprises the neutral conductor cable 15, the test electrode 19 can couple to both neutral conductors 21, 22 to a sufficient capacitive extent and evenly.

The test electrode 19 comprises a test surface 26. The user of the surgical instrument 11 brings the instrument 11 into the vicinity of the test surface 26, so as to test the spark starting ability and any other operability of the instrument 11. In the embodiment of FIG. 3a, the test electrode 19 comprises a cohesive test surface 26. The test surface 26 can be cleaned particularly well in this manner.

FIG. 4a as well as FIG. 3 shows a neutral conductor cable 15 comprising a test electrode 19, which is ring-shaped, but which comprises a convex test surface 26, which is curved outwards in this case. The test surface 26 is also cohesive. The test electrode 19 can be cleaned easily due to the two-dimensional shape, that is, due to the fact that it is curved outwards in two directions, and also due to the cohesive surface. The user of the instrument test arrangement 18 can furthermore always see the relative position of the probe and of the test electrode 19 when carrying out the instrument test, and, if desired, he can rule out that he touches the test electrode 19 with the probe 11 and possibly contaminates it.

A ring-shaped test electrode 19, e.g. a test electrode as illustrated in FIGS. 3 and 4a, can comprise an appendage 32, which sticks out transversely to the neutral conductor cable 15, for example a spherical, mushroom-shaped or door knob-shaped appendage 32 made of metal. A certain distance thus results between the neutral conductor cable 15 and the test surface 26, which is arranged at the appendage 32. An example for a test electrode comprising an appendage 32 and a ring is illustrated in FIG. 4b.

Figure 5:
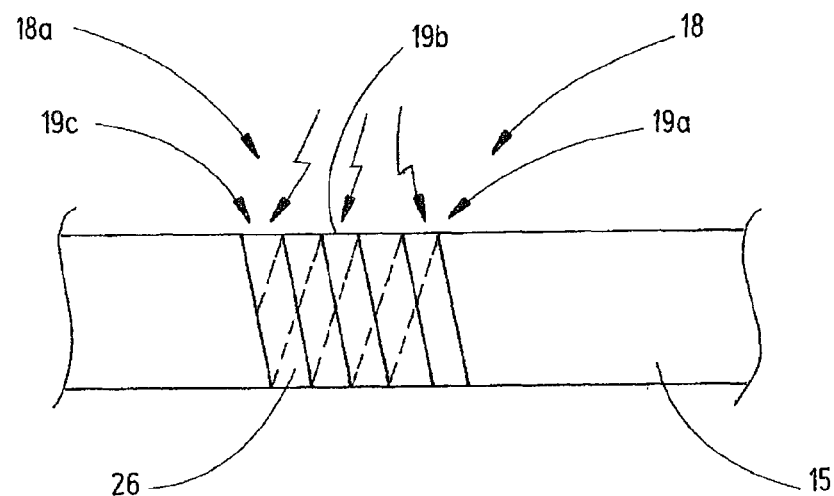

The neutral conductor cable 15 illustrated in FIG. 5 is surrounded by an alternative helical test electrode 19, which is embodied in a helical spring-type manner. The test electrode 19 can act through a metal band, which follows a helical line, metallization or foil. Due to the helical design of the test electrode 19, a particularly flexible test electrode can be created, which hardly interferes with the flexibility of the neutral conductor cable 15. The coupling of the test electrode 19 to the neutral conductors 21, 22, in turn, can take place capacitively with the cable insulation as dielectric or in any other manner described in this document.

From the perspective of the spark, as suggested in the figure, the test electrode 19 in FIG. 5 presents itself like two or more test electrodes 19a, b, c, which are connected to one another galvanically. Reference can also be made here to parts or sections, which are connected to one another conductively, of a single test electrode.

Figure 6:
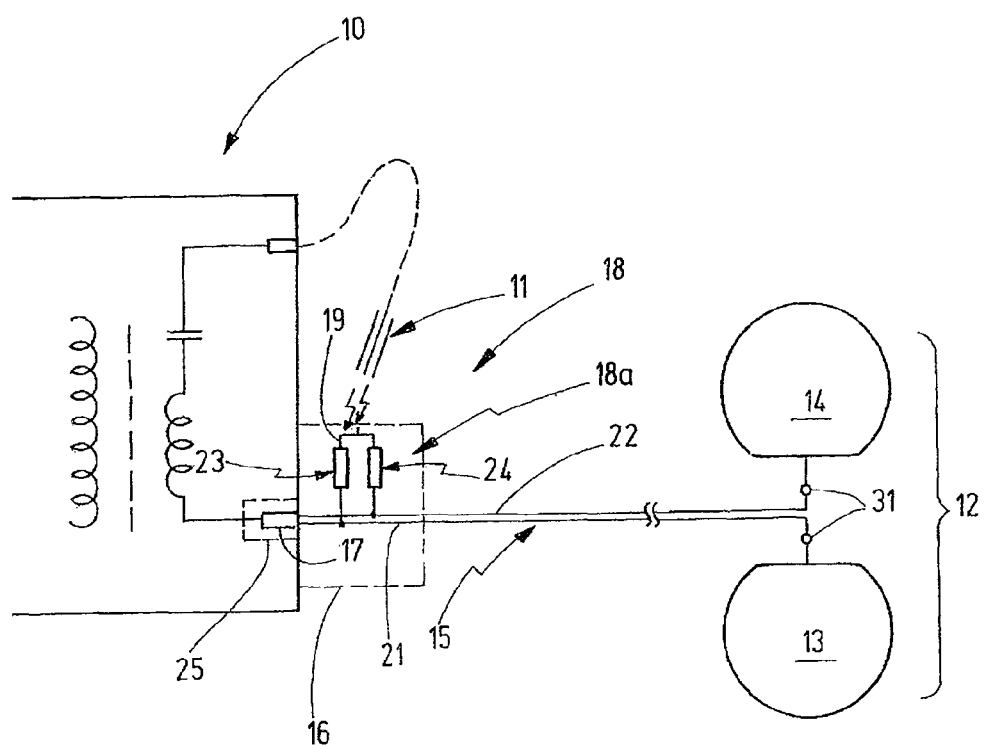
FIGS. 6 to 10 show further embodiments of the instrument test arrangement.
Figure 11:
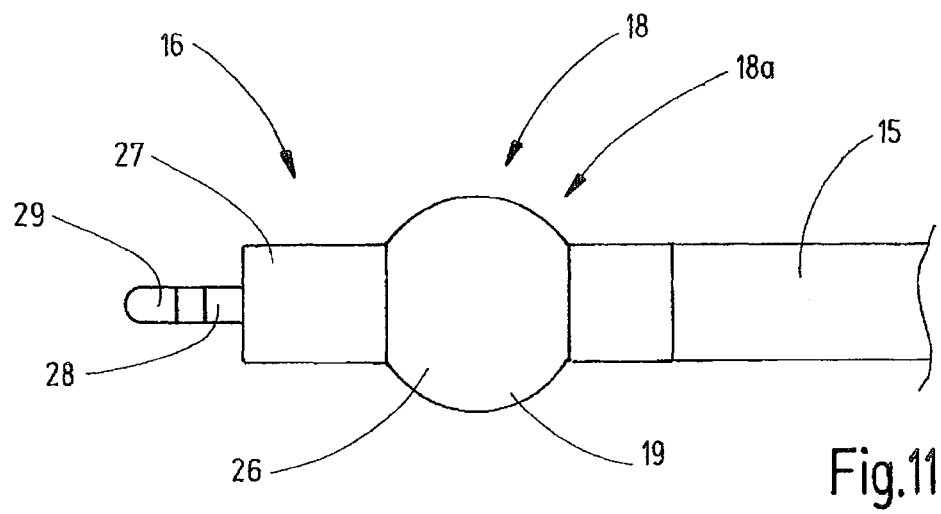
FIGS. 11 to 13 show specific embodiments of the embodiments according to FIGS. 6 to 9.

FIG. 6 illustrates an instrument test arrangement 18 comprising a test electrode 19 in a connector 16, which is suggested schematically in FIG. 2 in a dashed manner. An exemplary embodiment of the connector is illustrated in FIG. 11. The connector 16 comprises a body 27. The body 27 is enveloped by a metal ring, which forms the test electrode 19. The ring is additionally curved in longitudinal direction of the connector 16, so that a two-dimensionally curved cohesive test surface 26 is formed.

In the case of the above-described exemplary embodiments, the test electrode 19 preferably couples evenly through the insulator body 27, capacitively to the neutral conductors 21, 22, which are arranged in the neutral conductor cable 15 or the plug of the neutral conductor cable, respectively. For example, the coupling or connection, respectively, of the neutral electrode to the neutral conductors 21, 22, however, can also take place by means of capacitive components, which can be arranged in the insulator body 27. The plug 16 comprises contacts 28, 29 of a connector pin, which projects away from the connector 16, which contact the neutral conductors 21, 22. When in use, the connector pin is inserted into the neutral electrode socket 17 of the device 10. Apart from that, the descriptions for the other embodiments apply.

Figure 7:
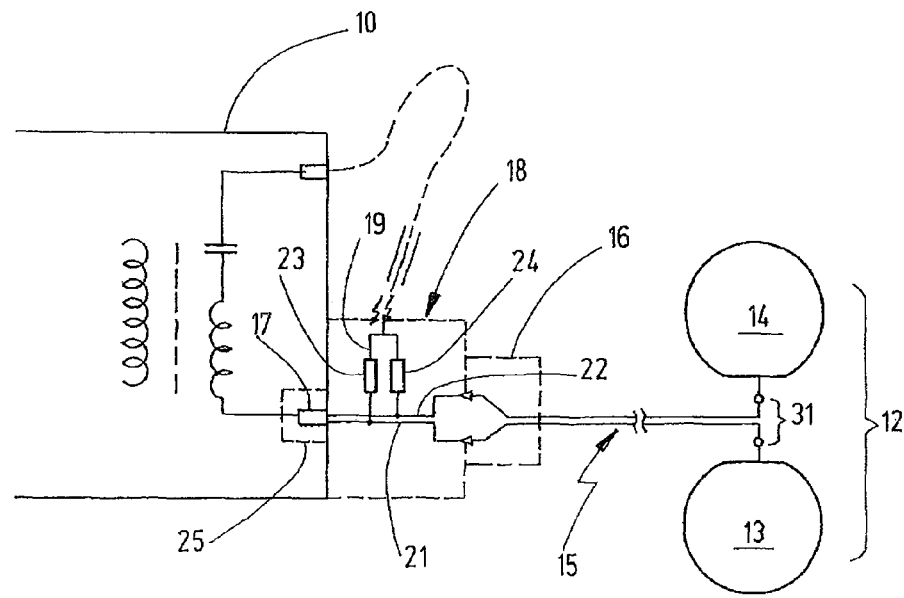
Figure 12:
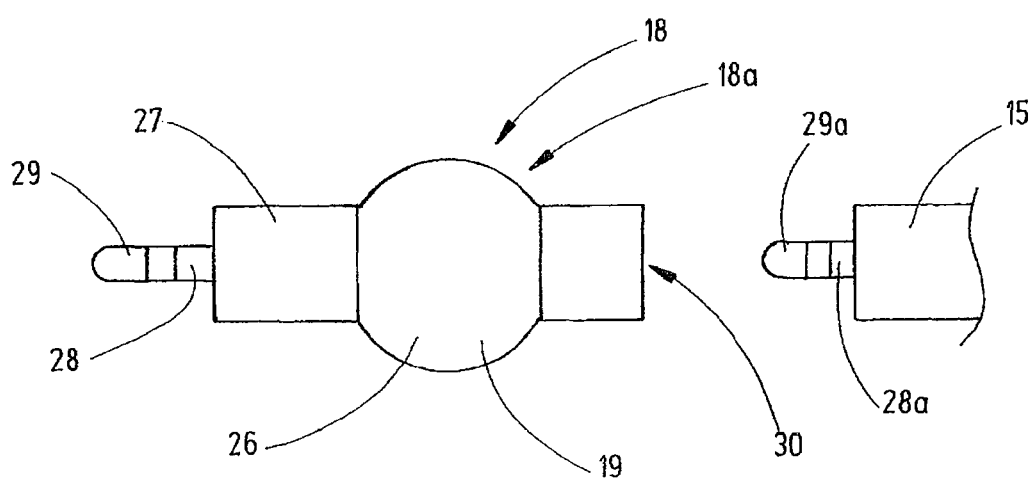

In a further embodiment according to FIG. 7, the instrument test arrangement 18 is embodied as plug adapter, which can be arranged between the connector 16 and the neutral socket 17. An example for the plug adapter, which is illustrated schematically in FIG. 7, is shown in FIG. 12. The plug adapter comprises an insulator body 27, on which a ring-shaped test electrode 19 is arranged. The test electrode 19 is embodied similar to the corresponding electrode in the subject matter from FIG. 11. In particular, it comprises a convex curvature in longitudinal direction of the plug, so that a curvature of the test surface 26, which is two-dimensional as a whole, is attained. For example, the test electrode 19 couples evenly in a capacitive manner via capacitors or via the insulator body 27 to extensions of the neutral conductors 21, 22, which are arranged in the plug adapter and which are connected to the contacts 28, 29. On the side located opposite the connector pin, the plug adapter comprises a socket 30, which comprises contacts, which contact the neutral conductors, which run in the plug adapter. At one end, the neutral cable 15 comprises a connecting device comprising a connector pin comprising contacts 28a, 29a. The connector pin is plugged into the socket 30, so that the electrode patches 13, 14 are connected to the device 10. Apart from that, the descriptions for the other embodiments apply.

Figure 8:
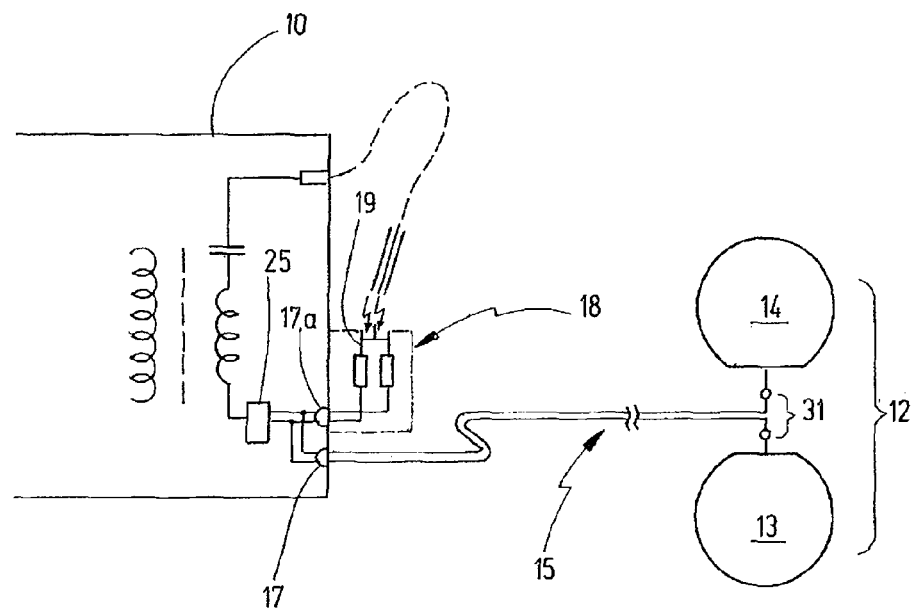
Figure 13:
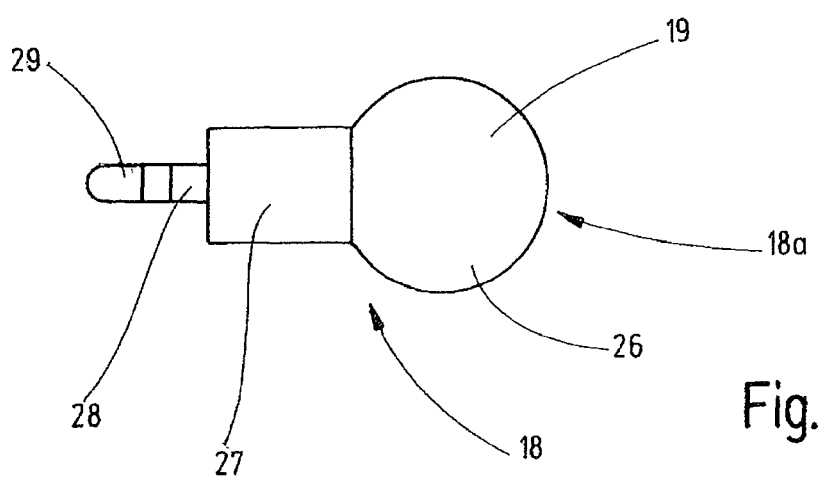

FIG. 8 illustrates an instrument test arrangement 18 according to a further embodiment of the invention. A separate socket 17a, which is connected electrically parallel to the socket 17, is embodied at the device. The instrument test arrangement 18 can, in turn, be plugged into this separate socket 17a. FIG. 13 shows an example for such a spark or arc striking test plug. The instrument test arrangement 18, in turn, comprises a connector pin comprising contacts 28, 29, which in each case couple capacitively to the knob-shaped electrode 19, which is arranged at an end of the insulator body 27 located opposite the connector pin. Apart from the special features of this embodiment, the descriptions already provided in context with other embodiments apply.

Figure 9:
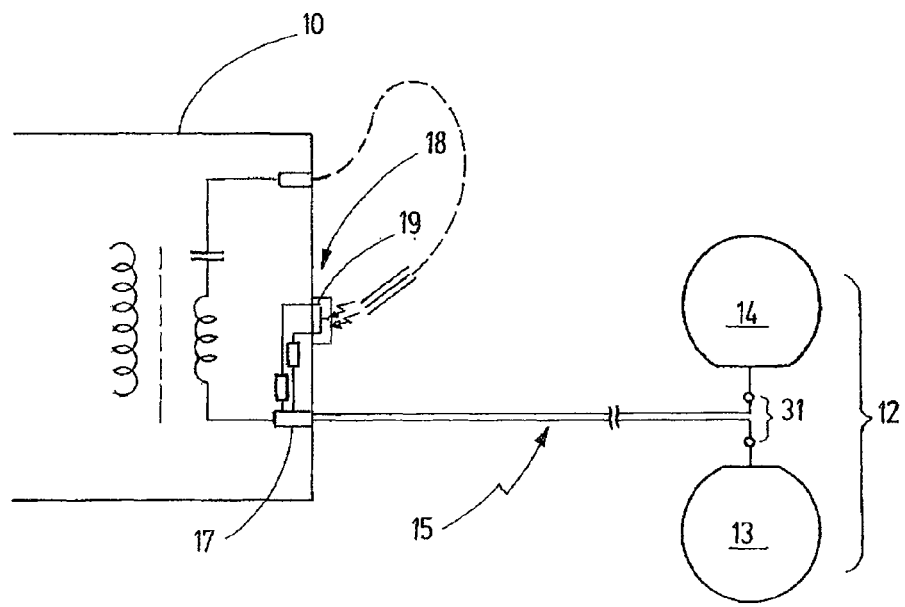
Figure 10:
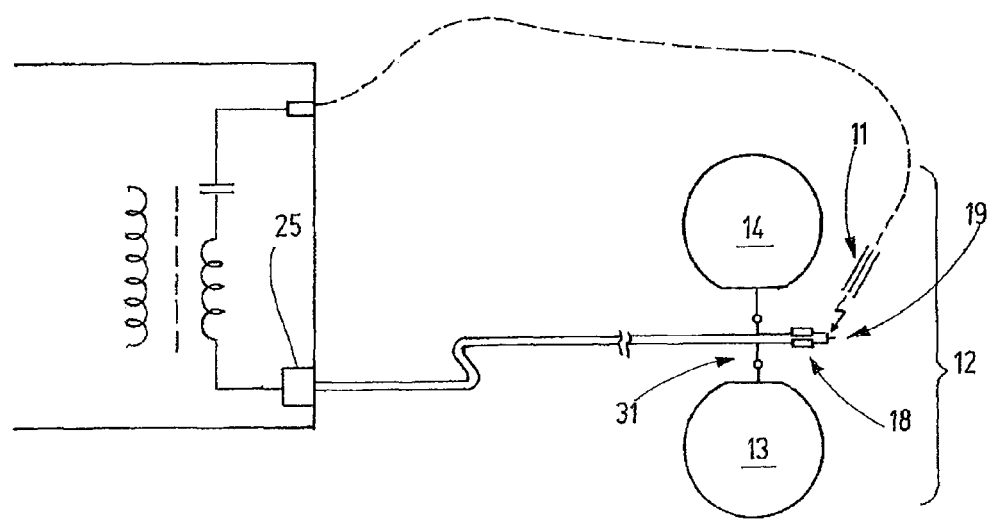

It is also possible to install the instrument test arrangement 18 into the device 10, as illustrated in FIG. 9. For example, the test electrode 19 can be curved in a knob-shaped or spherical manner, as in the subject matter of FIG. 13. Reference is additionally made to the description above.

It is also possible to arrange the instrument test arrangement 18 at the neutral electrode arrangement 12, for example at the neutral electrode connection 31. The instrument test arrangement 18 can comprises its own insulator housing or, e.g., can be arranged in the neutral electrode connection 31. Apart from the special features of this embodiment, the descriptions already provided in context with other embodiments, apply in turn.

An instrument test arrangement 18 is specified, which is preferably equipped for medical instruments 11 for argon plasma coagulation. The instrument test arrangement 18 comprises an electrode arrangement 18a, comprising at least one test electrode 19. In a preferred embodiment, a test electrode is thereby connected to two neutral conductors 21, 22 of a neutral conductor cable 15 or device 10, wherein the neutral conductors 21, 22 are insulated from one another, and wherein the first coupling impedance 23 between the test electrode 19 and the first neutral conductor 21 and the second coupling impedance 24 between the test electrode 19 and the second neutral conductor 22 are equal or at most slightly different, so that a split circuit 25, which is assigned to a neutral electrode arrangement 12, does not trigger due to the strike of a test spark or arc.

The invention claimed is:

1. An instrument test arrangement, in particular for medical instruments for argon plasma coagulation, comprising:
   an electrode arrangement configured to test a medical instrument, the electrode arrangement comprising at least one spark striking test electrode, which is connected electrically to a neutral conductor of a neutral conductor cable or of a device,
   wherein the neutral conductor cable or the device comprises two neutral conductors, which are insulated from one another and are connected to two partial electrodes of a neutral electrode arrangement, wherein the partial electrodes are connected to a split circuit which serves the purpose of measuring the electrical resistance between the two partial electrodes to detect whether the partial electrodes comprise sufficient electrical contact to the patient, and
   wherein the spark striking test electrode couples to the neutral conductors with the same coupling impedances or with coupling impedances that are at most slightly different, so that when HF energy is applied to the spark striking test electrode this does not result in currents in the neutral conductors which are different to the extent that the split circuit erroneously indicates a lack of contact of the partial electrodes to the body of the patient.

2. The instrument test arrangement of claim 1, wherein the spark striking test electrode at least partially comprises the neutral conductor cable.

3. The instrument test arrangement of claim 1, wherein the spark striking test electrode is a metallic ring or a sleeve.

4. The instrument test arrangement of claim 1, wherein the spark striking test electrode is a metal foil, a wire, a metallization and/or a metal coating.

5. The instrument test arrangement of claim 4, wherein the spark striking test electrode is embodied as a screw helix, the coils of which comprise the insulation of the neutral conductor cable.

6. The instrument test arrangement of claim 1, wherein the spark striking test electrode is connected to the neutral conductor via a component, which comprises an impedance.

7. The instrument test arrangement of claim 1, wherein the spark striking test electrode is connected to a first neutral conductor via a first component, which comprises a first impedance, and is connected to a second neutral conductor via a second component, which comprises a second impedance, wherein the first and the second component comprise the same electrical characteristic values.

8. The instrument test arrangement of claim 1, wherein the total capacitance between the neutral conductors in the instrument test arrangement is less than or equal to 1 nF.

9. The instrument test arrangement of claim 1, wherein the electrode arrangement is arranged at a flexible neutral conductor cable between a connector and a neutral electrode arrangement or a neutral electrode connection.

10. The instrument test arrangement of claim 1, wherein the spark striking test electrode comprises a convex test surface.

11. The instrument test arrangement of claim 1, wherein the spark striking test electrode comprises a cohesive test surface.

12. The instrument test arrangement of claim 1, wherein a capacitive coupling couples the spark strike testing electrode and the neutral conductors.

13. The instrument test arrangement of claim 12, wherein the capacitive coupling is configured to guide a current via the two neutral conductors to the neutral conductor cable or device when a test spark strikes the spark striking test electrode.

\* \* \* \* \*